United States Patent [19]
Young

[11] Patent Number: 5,125,835
[45] Date of Patent: Jun. 30, 1992

[54] DENTAL SYRINGE WITH FINGER ACTUATED TIP RETAINER ASSEMBLY

[75] Inventor: Barry S. Young, Tualatin, Oreg.

[73] Assignee: Dental Components, Inc., Newberg, Oreg.

[21] Appl. No.: 720,418

[22] Filed: Jun. 25, 1991

[51] Int. Cl.⁵ .................... A61G 17/02; A61C 1/10; A61C 1/12; A61C 17/02
[52] U.S. Cl. ...................... 433/80; 433/85; 433/88
[58] Field of Search .............. 433/80, 84, 85, 88, 433/126; 604/30, 199, 246, 257, 258, 261

[56] References Cited

U.S. PATENT DOCUMENTS

| | | | |
|---|---|---|---|
| 3,511,235 | 8/1967 | Stran | 433/80 |
| 4,026,025 | 5/1977 | Hunt | 433/80 |
| 4,248,589 | 2/1981 | Lewis | 322/80 |
| 4,517,962 | 5/1985 | Heckele | 128/6 |
| 4,957,483 | 9/1990 | Gonser et al. | 604/30 |
| 4,975,054 | 12/1990 | Esrock | 433/80 |

*Primary Examiner*—Cary E. O'Connor
*Assistant Examiner*—Cindy A. Cherichetti
*Attorney, Agent, or Firm*—James D. Givnah, Jr.

[57] ABSTRACT

A dental syringe is disclosed having a head and attached handle. Finger actuated valves in the head control water and air flows to a syringe tip having concentric conduits. A tip retainer assembly includes a holder having a socket to insertably receive the syringe tip. A lock collar, slidably carried by said holder, has a conical surface which acts on ball elements in the holder to urge them into locking engagement with a grooved, inserted portion of the syringe tip. A spring automatically positions the collar to the locking position with movement of the collar in an opposite direction to a tip unlocking position by fingertip pressure applied to the collar.

14 Claims, 1 Drawing Sheet

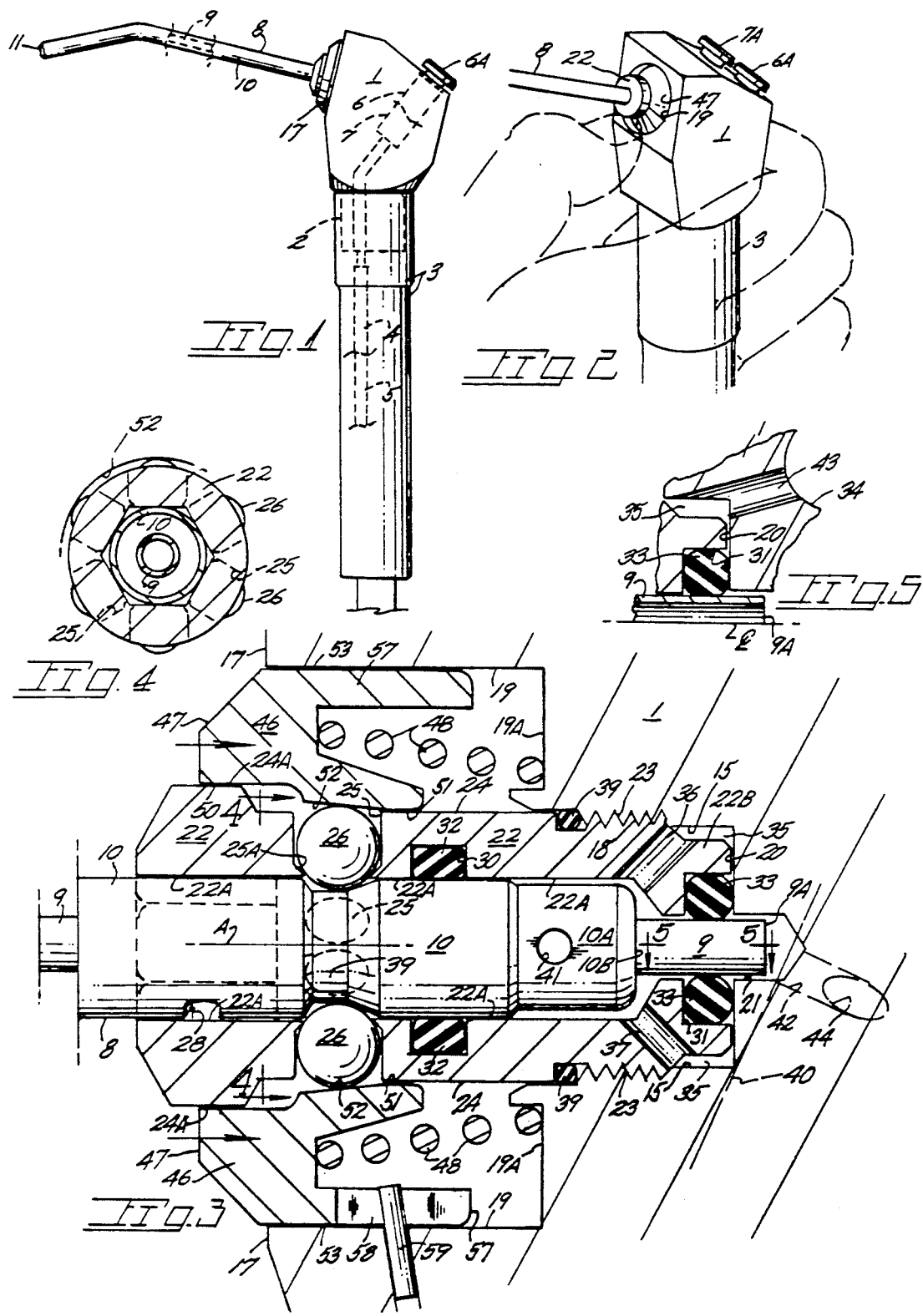

DENTAL SYRINGE WITH FINGER ACTUATED TIP RETAINER ASSEMBLY

BACKGROUND OF THE INVENTION

The present invention pertains generally to handheld devices capable of discharging fluids, singly or combined, through a detachable tip.

In wide use for many years in the dental profession are handheld devices for discharging pressurized air and water flows into the mouth. Such devices typically include concentric conduits, termed a tip, for water and air flows with the conduits terminating at a discharge point remote from a handle of the device. Such tips are detachable as they must be sterilized prior to use with a new patient. Accordingly, several times a day, a dentist or technician must change the syringe tip and over the course of the day, considerable effort is expended in tip removal and replacement as types of dental syringes often utilize threaded components to secure syringe tip in place in the syringe head. Commonly, a tool is required for tip removal for the backing off of a nut element and subsequent proper tightening of same which are repeated several times during the course of a day.

Another consideration that must be given to securing a syringe tip in place in the syringe head is the prevention of accidental tip ejection during syring use. As pressurized air and water flows are applied to the rearward end of the syringe tip, it is important that the connection between the tip and the syringe head be a positive one to avert the risk of tip loss. Further, it is desirable that tip securement be achieved without reliance on resilient components susceptible to deterioration or wear. Examples of dental syringes utilizing threaded collet elements for tip attachment are found in U.S. Pat. Nos. 4,957,483, 4,248,589 and 4,026,025 to mention a few. U.S. Pat. No. 4,975,054 utilizes a spring clip for tip retention.

SUMMARY OF THE INVENTION

The present invention is embodied within a retainer assembly to detachably mount a syringe tip on the syringe head utilizing spring biased locking means.

A syringe head defines passages through which air and water flows are controlled by finger actuated valves to provide singular or combined flows to the syringe tip structure. The syringe head defines a bore to receive the present tip retainer assembly. A tip holder of the assembly carries ball elements circumposed about a socket in the holder into which an end of the tip is inserted. The ball elements are urged inward into tip engagement and specifically into a recessed portion of the tip to lock same in place. A lock collar in place about the holder acts on the ball elements and is automatically biased toward a locking position. For tip release, the collar is displaced rearwardly to release the ball elements. A face of the collar is disposed for fingertip contact. Accordingly tip release is accomplished without a wrench or release tool or time-consuming manipulation of a threaded element. The socket in the tip holder may be partially defined by tool receiving surfaces for purposes of holder installation and removal from the syringe head during initial assembly.

Important objectives include the provision of a dental syringe having a tip retainer assembly locked and unlocked by a yieldably mounted, finger actuated collar; the provision of a tip retainer assembly for receiving a dental syringe tip which utilizes a series of ball elements to positively lock the syringe tip against axial movement while permitting unlocking by finger pressure on a collar face; the provision of a retainer assembly including a collar shaped locking element having a conical surface automatically biasing ball elements into tip locking engagement; the provision of a syringe tip retainer assembly which avoids the use of an O-ring to perform a locking function which renders such a function susceptible to failure and tip ejection in the event of O-ring deterioration or failure; the provision of a tip retainer assembly of few components to enable low manufacture and assembly costs; the provision of a syringe tip retainer assembly which permits tip removal and replacement without use of a tool to promote frequent tip changing for infection control purposes.

BRIEF DESCRIPTION OF THE DRAWINGS

With continuing attention to the drawings:

FIG. 1 is a side elevational view of a dental syringe provided with the present tip lock;

FIG. 2 is a fragmentary perspective view of the syringe during removal of the tip;

FIG. 3 is a vertical medial sectional view of the tip retainer assembly housed within a syringe head;

FIG. 4 is a vertical sectional view taken along 4—4 of FIG. 3; and

FIG. 5 is a horizontal sectional view taken downwardly along line 5—5 of FIG. 3.

DETAILED DESCRIPTION OF THE PREFERRED EMBODIMENTS

With continuing attention to the drawings wherein reference numerals indicate parts similarly hereinafter identified, the reference numeral 1 indicates a syringe head having a threaded boss 2 for detachable engagement with a tubular handle at 3. In typical fashion the syringe head is served by pressurized water and air lines at 4 and 5. Finger operated water and air valve assemblies at 6 and 7 are suitably secured within bores in the syringe head 1 with each valve assembly equipped with a push button control at 6A and 7A. Passages in the head communicate the lines 4 and 5 with the valve assemblies. Later described passages in head 1 serve to communicate the valve assemblies 6 and 7 with syringe tip at 8 having inner and outer concentric conduits at 9 and 10 which discharge in either a singly or combined manner at an outlet 11. The foregoing description is intended to be generally applicable to known dental syringe construction.

With attention now to FIG. 3, syringe head 1 is provided with a bore 15 internally threaded at 18 for a portion of its length and which terminates in a rear wall 20 provided with a central recess 21. A counterbore 19 terminates in a rear wall 19A. A head frontal wall is at 17.

A tip retainer assembly includes a tip holder 22 threaded at 23 adjacent its inner end for engagement with head internal threads at 18. Holder 22 defines a socket 22A for tip reception while a cylindrical outer wall 24 slidably receives a later described collar. The holder is provided with radial bores at 25 within each of which is received a ball element 26. Inner lip 25A limits inward movement of the ball element 26 in the absence of an inserted tip 8 in socket 22A. A forward portion of socket 22A is defined by flats as at 28, as by broaching of the socket surface to provide tool receiving surfaces to enable driving of holder 22 with a wrench type tool during initial tool assembly. Holder 22 is provided with an inner groove at 30 to receive an O-ring 32 while an O-ring at 33 is confined in an end recess at 31. If desired, O-ring 33 may be inset into a shouldered area of head recess 21 to prevent a water flow along the exterior of tip conduit 10. An additional O-ring at 39 is carried by holder 22 for sealing contact with head 1 to prevent air leakage. The O-rings are of elastomeric material.

The inner or rearward end segment 22B of tip holder 22 is of reduced diameter to provide a space 35 for pressurized air from a head defined air passage at 43 in FIG. 5. Air from space 35 is routed into socket 22A by holder passageways 36 and 37. The airflow is controlled by finger actuated valve 7 mounted in a head cavity 34.

Outer conduit 10 of tip structure 8 has an annular groove 39 formed adjacent its inserted end. Groove 39 receives ball elements 26 and is of a depth leaving an annular space about inner conduit 9 so as not to obstruct an airflow moving along and between the conduits which enters the tip structure at an aperture 41. Outer conduit 10 terminates rearwardly in a somewhat reduced diameter segment 10A which terminates at an inner end 10B soldered to the outer periphery of inner conduit 9 in a airtight manner. Inner conduit 9 receives a water flow at its rearward open end 9A from a passage 42 in the head served by an inlet orifice 44 in the wall of cavity 40 in the syringe head which receives water flow control valve 6. Water is discharged through orifice 44, as controlled by valve 6, and flows through passageway 42 toward end 9A of conduit 9.

With attention now back to the tip retainer assembly, slidably disposed on holder 22 is a lock collar 46 of the tip retainer assembly with the collar having a frontal wall 47 to receive finger imparted force for momentary rearward displacement of the collar against the action of a spiral compression spring 48. Spaced apart, first and second internal wall surfaces at 50 and 51 of the collar are in sliding engagement with holder external walls 24A and 24. Wall surface 50 defines an annular space to receive the ball elements. Intermediate said internal walls of the collar is a rearwardly tapering, conical inner wall surface 52 which imparts inward radial movement to ball elements 26 coincident with outward or forward movement of the collar in response to spring 48. An outer wall 53 of the collar 46 is located on a perimetrical flange 57 of the collar which is slotted at 58 to receive a head carried anti-rotation pin 59 acting on the collar to prevent movement about the longitudinal axis A of holder 22. Accordingly, rotation of syringe tip 8 about its major axis is inhibited somewhat so that the angulated end segment of the tip may be manually positioned or set about the axis (coaxial with holder axis A) by the user as for example when the tip structure is used to momentarily displace the patient's cheek. With holder 22 being stationary and with collar 46 prevented from rotating,/rotation is inhibited by the friction of ball elements 26 in wiping engagement either with tip groove 39 or with collar conical wall 52 supplemented by tip engagement with O-ring seals 32 and 33.

Several variations may readily come to mind to those knowledgeable of dental syringes, one such being the forward elongation of holder 22 to permit forward offsetting of lock collar 46 from the front wall 17 of the syringe head to dispense with counterboring of the head and to utilize but a single internally threaded bore, such as found on prior art dental syringes.

Operation of the present syringe is believed to be apparent from the foregoing description. Periodic tip removal is readily accomplished by fingertip pressure on collar 46 with simultaneous extraction of tip structure 8 accomplished by the user's remaining hand. Conversely, installation of tip structure 8 is readily accomplished by momentary depressing of collar 46 to permit passage of the inserted end of tip structure 8 past ball elements 26. With the collar forward, the tip structure is securely locked against axial movement by the ball elements 26. The return of collar 46 to the forward or outward tip locking position is readily discernible by the user to provide verification the locked in place condition of the syringe tip.

While I have shown but one embodiment of the invention, it will be apparent to those skilled in the art that the invention may be embodied still otherwise without departing from the spirit and scope of the invention.

Having thus described the invention, what is desired to be secured by a Letters Patent is:

I claim:

1. In a dental syringe,
a head having fluid passages and defining first and second bores,
an elongate tip having multiple fluid conduits in communication with said bores, one of said conduits having a recessed segment,
a tip retainer assembly in said head insertably receiving one end of said tip, a holder having an inner wall defining a socket to insertably receive said tip, ball elements carried by said holder and positionable into said socket, a collar movably mounted on said holder and having an inner wall surface inclined to the collar axis for engagement with said ball elements when said collar is in a forward operative position to bias the ball elements into said socket and into biased engagement with the recessed segment of said tip to prevent tip displacement, a spring urging said collar toward said forward operative position, said collar having a frontal surface to receive a finger imparted force to urge the collar to a rearward inoperable position against the action of said spring to permit outward displacement of the ball elements by said tip during tip removal from the socket, said collar additionally defining a space into which the ball elements may move during tip removal from the holder.

2. The syringe claimed in claim 1 wherein said collar has first and second internal walls in sliding engagement with said holder.

3. The syringe claimed in claim 1 wherein said collar and said head include anti-rotation means to confine said collar against rotation during manual rotational positioning of the syringe tip and to thereafter inhibit random rotation of said tip during syringe use.

4. The syringe claimed in claim 1 wherein said frontal surface of the collar is normally offset outwardly from the head.

5. The syringe claimed in claim 1 wherein said holder defines radially directed bores each receiving one of said ball elements, said spring and said collar inner wall surface jointly acting to bias the ball elements radially into tip engagement.

6. In a dental syringe,
a head having fluid passages,
a handle attached to said head,
a tip with fluid conduit means in communication with said passages, said tip having a recessed segment, a tip retainer assembly carried by said head including a holder having a socket for tip reception, ball elements, radially directed bores in said holder each receiving one of said ball elements for travel into and out of said socket and into and out of engagement with said recessed segment of said tip, a collar disposed about a movable relative said holder and including a conical inner surface engageable with said ball elements to urge the elements into said socket and into engagement with said segment of said tip in said socket, resilient means biasing said conical inner surface of the collar into engagement with said ball elements to lock said tip in said holder, said collar having an exposed surface for the reception of finger pressure for displacement of said collar inner surface away from said ball elements to unlock said tip.

7. The syringe claimed in claim 6 wherein said collar has first and second internal annular walls in sliding engagement with said holder, said annular walls oppositely offset form said conical inner surface of the collar.

8. The syringe claimed in claim 6 wherein said head defines a bore and a counterbore to receive said holder and said collar, said counterbore terminating in an end wall, said resilient means embodied in a spiral compression spring in abutment at one of its ends with said end wall.

9. The syringe claimed in claim 6 wherein said recessed segment of said tip defines a groove into which said ball elements are biased by said resilient means.

10. A syringe tip retainer assembly for installation in a dental syringe, said assembly comprising in combination, an elongate holder defining a lengthwise directed socket for the inserted reception of a segment of a syringe tip, ball elements, radially directed bores in said holder, each of said bores receiving one of said ball elements, a lock collar slidably mounted for rectilinear travel on said holder and including an internal wall surface inclined to the collar axis and engageable with said ball elements during collar travel in one direction to bias said ball elements radially inward in their respective bores and into said socket and into engagement with a syringe tip in said socket, resilient means biasing said lock collar in said one direction, said lock collar having a surface for the application of finger imparted force for collar travel opposite to said one direction, means on said holder for seated retentive engagement with the dental syringe.

11. The tip retainer assembly claimed in claim 10 wherein said lock collar includes anti-rotation means to inhibit rotation of the syringe tip.

12. The tip retainer assembly claimed in claim 10 wherein said collar includes first and second internal annular walls in sliding engagement with said holder, said annular walls oppositely offset from said internal wall surface of the lock collar.

13. The tip retainer assembly claimed in claim 10 wherein said lock collar defines a slotted area to receive a pin carried by the dental syringe to prevent rotation of the lock collar for the purpose of inhibiting rotation of the syringe tip.

14. The tip retainer claimed in claim 10 wherein said ball elements are confined against rotational movement about a syringe tip by said holder, anti-rotation means acting on said lock collar, said ball elements in alternative wiping contact with said lock collar and the syringe to inhibit syringe/rotation tip.

* * * * *